(12) United States Patent
Hendriks et al.

(10) Patent No.: US 11,246,567 B2
(45) Date of Patent: Feb. 15, 2022

(54) INTRAVASCULAR DOPPLER ULTRASONIC DEVICE AND METHOD FOR CONTROLLING ITS OPERATION

(71) Applicant: KONINKLIJKE PHILIPS N.V., Eindhoven (NL)

(72) Inventors: Cornelis Petrus Hendriks, Eindhoven (NL); Arjen Van Der Horst, Tilburg (NL); Roland Alexander Van De Molengraaf, Geldrop (NL); Mark Thomas Johnson, Arendonk (BE); Franciscus Johannes Gerardus Hakkens, Eersel (NL); Daan Anton Van Den Ende, Breda (NL); Howard Alpert, El Dorado Hills, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 280 days.

(21) Appl. No.: 16/469,304

(22) PCT Filed: Dec. 14, 2017

(86) PCT No.: PCT/EP2017/082725
§ 371 (c)(1),
(2) Date: Jun. 13, 2019

(87) PCT Pub. No.: WO2018/109052
PCT Pub. Date: Jun. 21, 2018

(65) Prior Publication Data
US 2020/0022676 A1    Jan. 23, 2020

Related U.S. Application Data

(60) Provisional application No. 62/435,157, filed on Dec. 16, 2016.

(30) Foreign Application Priority Data

Feb. 21, 2017    (EP) ..................................... 17157129

(51) Int. Cl.
*A61B 8/00*    (2006.01)
*A61B 8/02*    (2006.01)
(Continued)

(52) U.S. Cl.
CPC ................ *A61B 8/445* (2013.01); *A61B 8/02* (2013.01); *A61B 8/12* (2013.01); *A61B 8/4466* (2013.01);
(Continued)

(58) Field of Classification Search
CPC .. A61B 8/445; A61B 8/02; A61B 8/12; A61B 8/4466; A61B 8/465; A61B 8/467;
(Continued)

(56) References Cited

U.S. PATENT DOCUMENTS

| 5,163,445 A | 11/1992 | Christian et al. |
| 6,764,441 B2 | 7/2004 | Chiel et al. |

(Continued)

FOREIGN PATENT DOCUMENTS

| WO | 1997044089 A1 | 11/1997 |
| WO | 2005011504 A1 | 2/2005 |

(Continued)

OTHER PUBLICATIONS

Radiology Key: Fastest Radiology Insight Engine, https://radiologykey.com/factors-that-influence-the-doppler-spectrum/, Accessed Jun. 2019.
(Continued)

*Primary Examiner* — Joel Lamprecht

(57) ABSTRACT

An intravascular Doppler ultrasonic device comprises a tip region forming a fraction of a catheter body at a distal end thereof and carrying an ultrasound probe. The tip region is
(Continued)

bendable in a direction perpendicular to a longitudinal direction. An actuator is provided in the tip region, which is configured to receive actuation drive power provided through the catheter body and to exert to the tip region a bending moment of a controllable amount. An actuation controller is configured to control actuation drive power delivery to the actuator so as to control the amount of the bending moment. A Doppler spectrum analysis unit is configured to receive Doppler spectrum data and to determine from it a Doppler signal quality measure indicative of a signal quality of the Doppler spectrum. The actuation controller is configured to determine the actuation drive power in dependence on the determined Doppler signal quality measure.

14 Claims, 6 Drawing Sheets

(51) Int. Cl.

| | | |
|---|---|---|
| *A61B 8/12* | (2006.01) | |
| *A61B 8/08* | (2006.01) | |
| *A61L 29/02* | (2006.01) | |
| *A61L 29/14* | (2006.01) | |
| *A61B 8/06* | (2006.01) | |

(52) U.S. Cl.
CPC .............. *A61B 8/465* (2013.01); *A61B 8/467* (2013.01); *A61B 8/488* (2013.01); *A61B 8/5223* (2013.01); *A61B 8/54* (2013.01); *A61L 29/02* (2013.01); *A61L 29/14* (2013.01); *A61B 8/06* (2013.01); *A61L 2400/16* (2013.01)

(58) Field of Classification Search
CPC ......... A61B 8/488; A61B 8/5223; A61B 8/54; A61B 8/06; A61B 8/4483; A61L 29/02; A61L 29/14; A61L 2400/16
See application file for complete search history.

(56) References Cited

U.S. PATENT DOCUMENTS

| | | | |
|---|---|---|---|
| 7,077,808 | B2 | 7/2006 | Couvillon, Jr. |
| 9,198,600 | B2 * | 12/2015 | Grunwald .............. A61B 8/461 |
| 10,219,780 | B2 * | 3/2019 | Castella ............... A61B 5/6852 |
| 2003/0216621 | A1 | 11/2003 | Alpert et al. |
| 2004/0056751 | A1 | 3/2004 | Park et al. |
| 2005/0027198 | A1 | 2/2005 | Couvillon, Jr. |
| 2009/0118612 | A1 | 5/2009 | Grunwald et al. |
| 2014/0066765 | A1 | 3/2014 | Fan et al. |
| 2018/0108827 | A1 | 4/2018 | Hakkens et al. |

FOREIGN PATENT DOCUMENTS

| | | |
|---|---|---|
| WO | 2006122001 A2 | 11/2006 |
| WO | 2013067025 A1 | 5/2013 |
| WO | 2014100402 A1 | 6/2014 |

OTHER PUBLICATIONS

International Search Report and Written Opinion, International Application No. PCT/EP2017/082725, dated Apr. 18, 2018.

* cited by examiner

INTRAVASCULAR DOPPLER ULTRASONIC DEVICE AND METHOD FOR CONTROLLING ITS OPERATION

CROSS-REFERENCE TO PRIOR APPLICATIONS

This application is the U.S. National Phase application under 35 U.S.C. § 371 of International Application No. PCT/EP2017/082725, filed on 14 Dec. 2017, which claims the benefit of U.S. Provisional Patent Application No. 62/435,157, filed on 16 Dec. 2016 and European Patent Application No. 17157129.2, filed on 21 Feb. 2017. These applications are hereby incorporated by reference herein.

FIELD OF THE INVENTION

The invention relates to an intravascular Doppler ultrasonic device, to a method for controlling operation of an intravascular Doppler ultrasonic device, and to a computer program for controlling operation of an intravascular Doppler ultrasonic device.

BACKGROUND OF THE INVENTION

WO 2013/067025 A1 describes devices, systems, and methods for controlling the field of view in imaging systems. In one embodiment an imaging system in the form of an intravascular Doppler ultrasonic device includes a flexible elongate member such as a catheter body, which extends along a longitudinal direction and is shaped for intravascular insertion into a blood vessel of a living being, an ultrasound probe forming an imaging transducer positioned within a tip region of the catheter body, an imaging marker positioned to be detectable within a field of view of the imaging transducer, and a controller in communication with the flexible elongate member and configured to adjust a control signal of the flexible elongate member based on the detection of the imaging marker in data received from the flexible elongate member in order to achieve a desired field of view for the imaging transducer.

WO 97/744089 describes a flexible, elongate probe having a distal end for insertion through physiological tissue, preferably through a lumen in the tissue. The probe includes a sensor, which generates signals indicative of a characteristic of the tissue in a vicinity of the probe, and an alignment mechanism which deflects the distal end of the probe in response to the signals. The signals may be indicative of obstructions or of the direction of a clear channel in the lumen. The sensor preferably comprises one or more ultrasound transducers.

U.S. Pat. No. 5,163,445 describes a system for measuring a characteristic of flow of liquid in a vessel of a patient comprising a transducer positioned in a vessel in a patient for supplying ultrasonic energy. The transducer produces a substantially uniform beam which encompasses the vessel. The transducer receives ultrasonic energy back scattered from the red blood cells and provides an electrical output signal. A first moment detector is provided which receives the electrical output from the transducer and provides a first moment signal. Normalization is provided to the output of the first moment detector to provide an electrical output representing a characteristic of the flow of the liquid in the vessel.

US 2003/0216621 A1 describes a multifunctional invasive cardiovascular diagnostic measurement host that interfaces a variety of sensor devices, such as guide wire-mounted pressure sensors, flow sensors, temperature sensors, etc, and provides a multi-mode graphical user interface providing a plurality of displays in accordance with the various types of sensors and measurements rendered by the sensors.

U.S. Pat. No. 7,077,808 B2 describes an ultrasonic imaging catheter apparatus and a method of using the same to scan the inner wall of a body lumen. The ultrasonic imaging catheter apparatus comprises a flexible elongate element adapted for insertion into a body lumen, the elongate element having distal and proximal ends; an ultrasonic transducer generating and detecting ultrasonic energy disposed proximate the distal end of the elongate element; a reflective member disposed proximate the ultrasonic transducer and optionally rotatable with respect to an axis of the body lumen, wherein the reflective member is adapted to reflect ultrasonic energy generated by the ultrasonic transducer to a wall of the body lumen and ultrasonic energy reflected by the wall back to the transducer; and an actuator, for example, an electroactive polymer actuator, adapted to change the angle of incidence of the ultrasonic energy relative to the reflective member.

SUMMARY OF THE INVENTION

It is desirable to improve adjustment of an intravascular Doppler ultrasonic device for achieving improved imaging results.

According to a first aspect of the present invention, an intravascular Doppler ultrasonic device comprises:
  a catheter body, which extends along a longitudinal direction and is shaped for intravascular insertion into a blood vessel of a living being;
  a tip region forming a fraction of the catheter body at a distal end thereof, the tip region being bendable in at least one direction perpendicular to the longitudinal direction;
  an ultrasound probe in the tip region, which is configured to emit ultrasonic radiation from the distal end of the catheter body in substantially the longitudinal direction and to receive ultrasound echo radiation from substantially the longitudinal direction and provide a probe signal indicative thereof;
  a Doppler spectrum determination unit, which is configured to receive the probe signal and to provide Doppler spectrum data indicative of a Doppler spectrum of the ultrasound echo radiation;
  an actuator in the tip region, which is configured to receive actuation drive power provided through the catheter body and to exert to the tip region a bending moment of a controllable amount;
  an actuation controller, which is configured to control power delivery to the actuator so as to control the amount of the bending moment;
  a Doppler spectrum analysis unit, which is configured to receive the Doppler spectrum data and to determine from it a Doppler signal quality measure indicative of a signal quality of the Doppler spectrum; wherein
  the actuation controller is further configured:
    to determine the actuation drive power in dependence on the determined Doppler signal quality measure, namely,
    to control a scanning motion of the tip region (106) within a predetermined scanning range by controlling the actuator (110) for consecutively setting a plurality of bending moments; and to determine the bending moment to be used for operation by selecting that bending moment which is associated with the determined Doppler signal quality measure that fulfils a predetermined Doppler spectrum selection criterion.

The intravascular Doppler ultrasonic device of the present invention allows determining a Doppler signal quality measure from Doppler spectrum data obtained from the received ultrasound echo radiation. It uses the determined Doppler signal quality measure for controlling the amount of the bending moment that bends the tip region in at least one direction perpendicular to the longitudinal direction of the catheter body. This way, a feedback mechanism is provided that allows adjusting the tip region for obtaining optimal Doppler spectrum data which may for instance be used for obtaining improved image information in ultrasound imaging.

Based on this, the intravascular Doppler ultrasonic device of the present invention provides an adjustment procedure that can be performed before or during operation of the device.

In the following, embodiments of the intravascular Doppler ultrasonic device will be described.

By storing operational parameter settings used for the different bending moment in the scanning process and subsequently selecting that setting that achieves the selected tip region orientation, the device can subsequently be operated with highest Doppler signal quality. The scanning motion can be performed in one or more planes, depending on the actuator design. Suitably, the scanning motion is performed back and forth.

The Doppler spectrum data is indicative of the Doppler spectrum of the received echo radiation. Suitably, the Doppler spectrum determination unit is configured to determine the Doppler spectrum from the received probe signal by a Fourier transform. Preferably, this is implemented by the Doppler spectrum determination unit being configured to perform a Fast Fourier Transform (FFT) algorithm using the probe signal as an input. The Doppler spectrum is suitably represented by the spectral power S of the received ultrasound echo radiation in dependence on the frequency f of the ultrasound echo radiation. In some embodiments, the Doppler spectrum determination unit is additionally configured to determine a further representation of the Doppler spectrum in the form of the spectral power S of the received ultrasound echo radiation in dependence on the velocity of an ultrasound scattering medium causing the ultrasound echo radiation. As is well known, the velocity can be determined from the Doppler frequency shift of the echo radiation with respect to a frequency of the emitted ultrasonic radiation.

The actuation drive power can be provided by controlling any suitable physical quantity that allows the actuator exerting a controllable amount of bending moment to the tip region in one or more directions. The actuation drive power can be provided for example by controlling an actuation drive voltage of controllable polarity and amount, or by controlling an electrical actuation drive current of controllable polarity and amount, or by controlling the amount of another physical quantity.

In another embodiment, the Doppler spectrum analysis unit of the intravascular Doppler ultrasonic device is configured to determine the Doppler signal quality measure at least once per cardiac cycle of the living being. In one variant of this embodiment, the actuation controller is configured to adjust the bending moment in a subsequent cardiac cycle if the Doppler signal quality indicator fulfills a predetermined adjustment criterion. The predetermined adjustment criterion can be selected according to the requirements of a given application case. In one variant, the adjustment criterion is related to an amount of the Doppler signal quality measure and for instance requires adjustment as soon as the amount of the Doppler signal quality measure falls below a predetermined amount, such as a certain threshold percentage of a reference amount of the Doppler signal quality measure which was previously measured. Such a reference amount can for example be determined as the maximum of the Doppler signal quality measure measured during a previous adjustment procedure. A suitable adjustment procedure is described hereinabove in the context of the previous embodiment.

In a group of different embodiments, the intravascular Doppler ultrasonic device has the Doppler spectrum analysis unit configured to determine the Doppler signal quality measure by determining and using at least one of the following quantities for calculating the Doppler signal quality measure from the Doppler spectrum S(f), which is derivable from the probe signal by a Fourier transform, suitably implemented in the form of a Fast Fourier Transform (FFT) algorithm and forms a representation of the spectral power S of the received ultrasound echo radiation in dependence on the frequency f of the ultrasound echo radiation:

a Doppler zeroth moment of the spectral power of the received ultrasound echo radiation a Doppler first moment of the spectral power of the received ultrasound echo radiation, a Doppler second moment of the spectral power of the received ultrasound echo radiation, a resistivity index, or a pulsatility index.

The Doppler zeroth moment is indicative of the signal power of the received ultrasound echo radiation.

The Doppler first moment depends on a mean velocity of the scattering medium, such as blood, whereas the Doppler second moment provides information on an angle of the tip region relative to an axis of a lumen of the blood vessel.

The resistivity index is sometimes also called resistance index and often abbreviated as RI. It is a measure of pulsatile blood flow that reflects the resistance to blood flow caused in a vascular region distal to the site of measurement.

The pulsatility index (PI) is equal to the difference between peak systolic velocity and the minimum diastolic velocity divided by the mean velocity during the cardiac cycle. As is well known, the blood velocity in arteries is higher during systole than during diastole. The pulsatility index decreases with increasing distance from the heart of the living being.

In other embodiments of the intravascular Doppler ultrasonic device, the ultrasound probe is configured to emit the ultrasonic radiation continuously and thus provide the probe signal continuously. This is used to advantage in an embodiment, wherein the actuation controller is configured to control a bending motion of the tip region so as to achieve a continuous scan across a range of different bending positions. In this embodiment, the Doppler spectrum determination unit is preferably configured to continuously provide Doppler spectrum data indicative of the Doppler spectrum data determined for the different bending positions. A Doppler spectrum selection unit is additionally provided in some variants, which is configured to select only that Doppler spectrum data which is associated with those bending positions that fulfill a predetermined Doppler spectrum selection criterion in terms of the Doppler signal quality measure.

Suitably a graphical user interface is additionally provided, which is configured to receive and display the selected Doppler spectrum data. This embodiment allows achieving that only images with a high Doppler signal quality measure are displayed on the graphical user interface.

In other embodiments of the present invention, the actuation controller is configured to control a bending motion of the tip region across a range of bending positions, to determine a motion response measure indicative of a difference between the Doppler signal quality measures determined at different ones of the bending positions, and to interpolate to an optimal velocity profile. The motion response measure can be of the form delta speed divided delta angle. Provided a geometry of the vessel and a position of the tip region in the vessel, and assuming that the velocity profile is parabolic, it is possible to determine the maximum speed in the vessel using the motion response measure.

Regarding the structural design of the intravascular Doppler ultrasonic device, the actuator preferably comprises an electrically controllable shape-changing material, which is mechanically coupled to the catheter body in the tip region and configured to cause the bending moment by a shape change in response to receiving the actuation power.

There are different alternative options which can be used to achieve a controllable orientation of the tip region of the catheter body within the vessel. These options can be implemented alone or in combination with each other. In one embodiment representing a first of these options, the actuator comprises at least one actuator layer made of an electroactive polymer material that is attached to a flat catheter core of the catheter body, and the actuator layer is configured to expand in-plane in response to receiving the actuation power. In another embodiment representing a second of these options, the actuator comprises at least one actuator wire made of a shape memory alloy that is attached to a catheter core. The actuator wire is configured to change its temperature in an amount that depends on an amount of actuation power received, and to change its shape in response to the temperature change. In another embodiment representing a third of these options, the actuator comprises at least one actuator layer made of a bi-metal that is attached to a flat catheter core of the catheter body, and the actuator layer is configured to expand in-plane in response to receiving the actuation power.

As an example of a combination of these optional features, the actuator of the intravascular Doppler ultrasonic device comprises in one embodiment at least one first actuator layer made of an electroactive polymer material that is attached to at least one second actuator layer made of a shape memory alloy.

According to a second aspect of the present invention, a method for controlling operation of an intravascular Doppler ultrasonic device is provided. The method comprises:
controlling emission of ultrasonic radiation by an ultrasound probe from a distal end of a catheter body in substantially a longitudinal direction of the catheter body, for receiving ultrasound echo radiation from substantially the longitudinal direction, and receiving a probe signal indicative thereof;
determining and providing Doppler spectrum data from the probe signal, the Doppler spectrum data being indicative of a Doppler spectrum of the ultrasound echo radiation;
controlling actuation drive power delivery to an actuator in a tip region forming a fraction of the catheter body at the distal end thereof, the tip region being bendable in at least one direction perpendicular to the longitudinal direction, so as to drive exertion of a bending moment of a controllable amount to the tip region; and wherein controlling power delivery comprises
receiving the Doppler spectrum data and determining from it a Doppler signal quality measure indicative of a signal quality of the Doppler spectrum,
determining the actuation drive power in dependence on the determined Doppler signal quality measure, namely,
controlling a scanning motion of the tip region (106) within a predetermined scanning range of different bending positions by controlling the actuator (110) for consecutively setting a plurality of bending moments; and
determining the bending moment to be used for operation by selecting (1210) that bending moment which is associated with the determined Doppler signal quality measure that fulfils a predetermined Doppler spectrum selection criterion.

The method of the second aspect of the invention shares the advantages of the device of the first aspect of the invention.

In one embodiment, the method further comprises
controlling a bending motion of the tip region for continuously scanning across the scanning range;
continuously providing the Doppler spectrum data determined for the different bending positions;
selecting only that Doppler spectrum data which is associated with that bending position which is associated with the determined Doppler signal quality measure indicative of the highest Doppler signal quality; and
controlling display of the selected Doppler spectrum data via a graphical user interface.

According to a third aspect of the invention a computer program is provided, comprising executable code for executing the method of the second aspect or one of its embodiments when executed by a processor of a computer.

It shall be understood that the intravascular Doppler ultrasonic device of claim 1, the method of claim 12 for controlling operation of an intravascular Doppler ultrasonic device, and the computer program for controlling operation of an intravascular Doppler ultrasonic device of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The Doppler spectrum of a blood vessel provides information about its hemodynamics which is important in the diagnosis of arterial disease, e.g., stenosis or micro-vascular disease. An intravascular Doppler measurement can be carried out with a catheter or wire containing an ultrasound element at the tip of the device. The following description of an intravascular Doppler ultrasonic device refers to FIGS. 1 to 3 in parallel.

Figure 1:
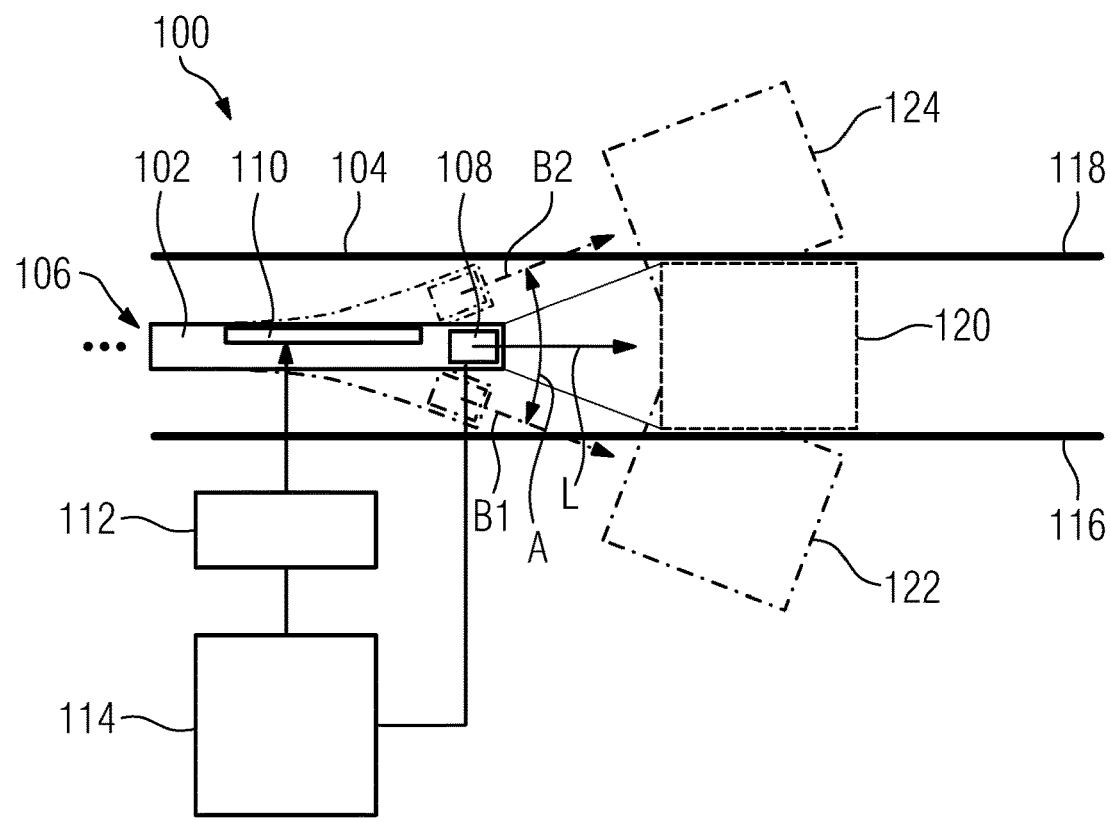
FIG. 1 is a schematic illustration of an intravascular Doppler ultrasonic device in accordance with an embodiment of the present invention.
Figure 2:
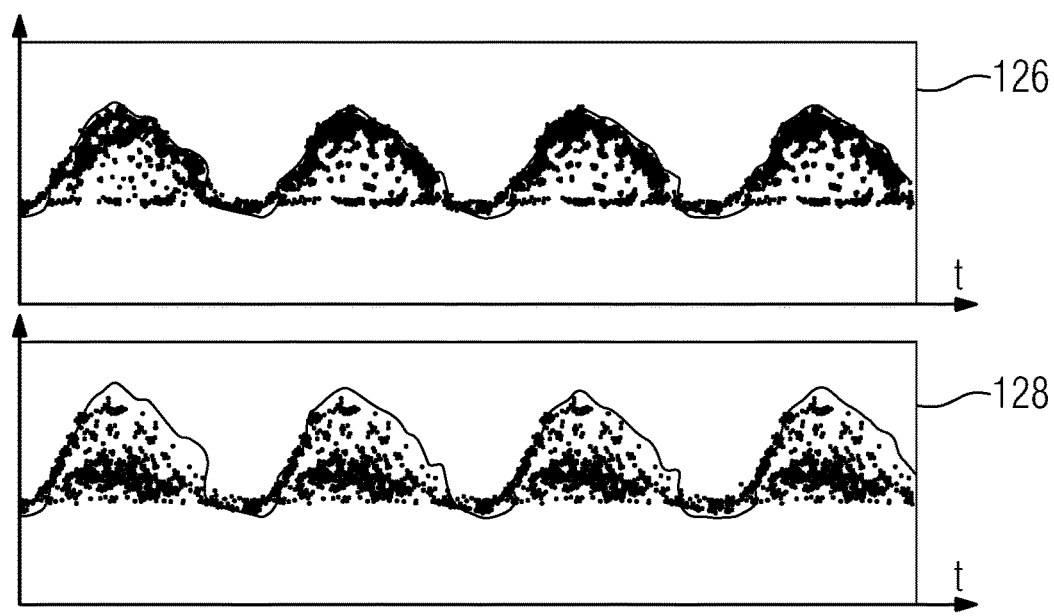
FIG. 2 illustrates a display of Doppler spectrum data obtained at different bending settings of the tip region of the intravascular Doppler ultrasonic device of FIG. 1.
Figure 3:
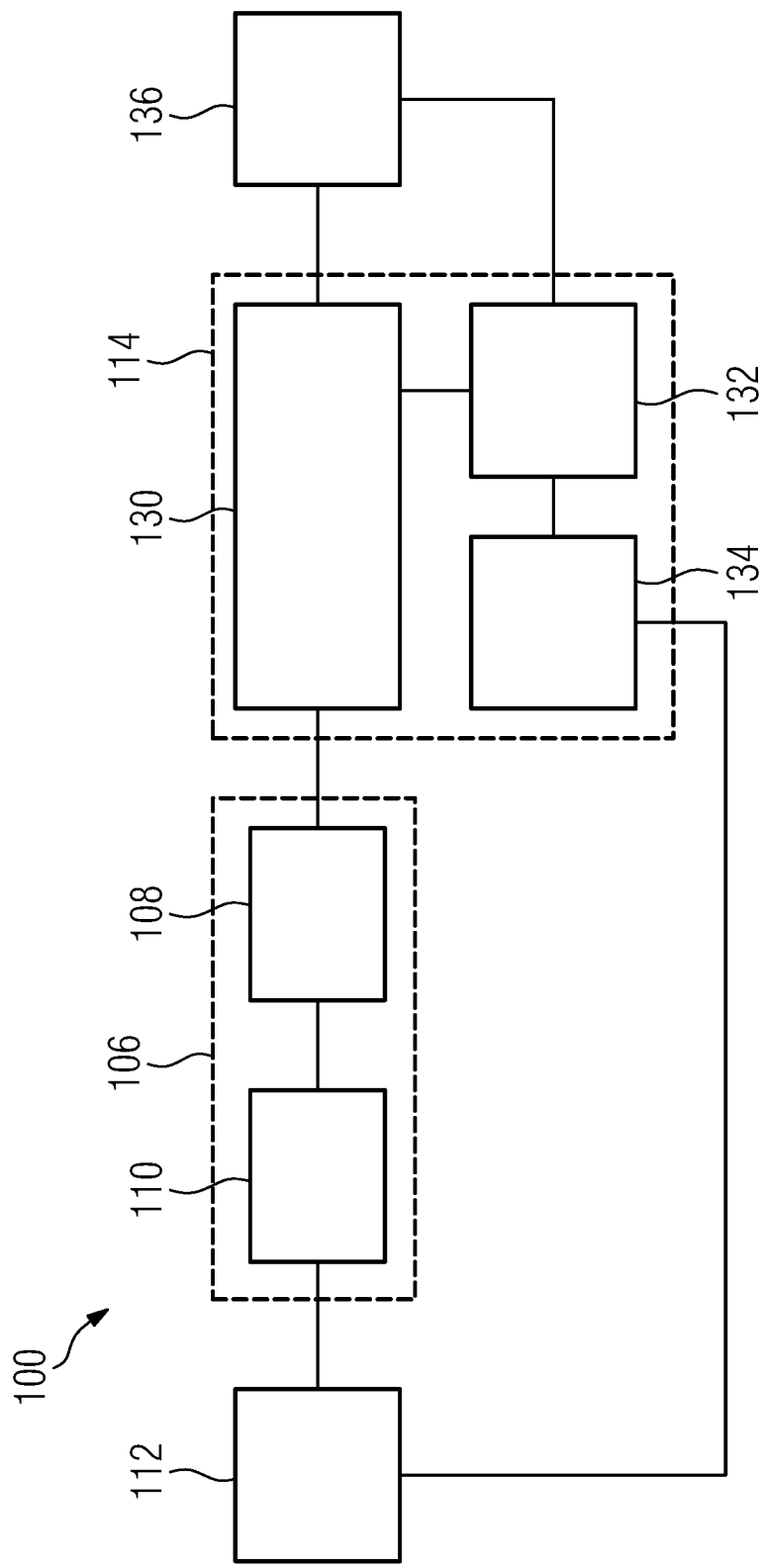
FIG. 3 is a block diagram of the intravascular Doppler ultrasonic device of FIG. 1.

FIG. 1 is a schematic illustration of an intravascular Doppler ultrasonic device 100 in accordance with an embodiment of the present invention. FIG. 2 illustrates a display of Doppler spectrum data obtained at different bending settings of the tip region of the intravascular Doppler ultrasonic device 100 of FIG. 1. FIG. 3 is a block diagram of the intravascular Doppler ultrasonic device 100 of FIG. 1.

The intravascular Doppler ultrasonic device 100 comprises a catheter body 102, which extends along a longitudinal direction L and is shown here during intravascular insertion into a blood vessel 104 of a living being. The catheter body 102 has a tip region 106 that forms a fraction of the catheter body 102 at a distal end thereof. The tip region 106 includes an ultrasound probe 108, which is configured to emit ultrasonic radiation from the distal end of the catheter body 102 in substantially a longitudinal direction L of the catheter body, and to receive ultrasound echo radiation from a sample area 120 located substantially the (inverted) longitudinal direction and provide a probe signal indicative thereof. The ultrasound probe typically receive electrical power to perform its function but other ways of powering may be used, e.g. optical. The measured probe signal typically provides information on a time span between emitting the ultrasonic radiation and receiving back the ultrasound echo radiation, which thus comprises information on a distance between the ultrasound probe and a structure or particle backscattering the emitted ultrasonic radiation.

The sample area 120 extends over the full diameter of the blood vessel 104 in the present illustrative example. However, that is not a requirement. Depending on an application case, the aperture of the ultrasound radiation can be smaller and thus render the sample area smaller in diameter than the blood vessel. The probe signal thus provides information on a velocity profile of particles flowing in the blood vessel and scattering the ultrasound radiation back to the ultrasound probe 108.

Good alignment of the tip region 106 with respect to the blood vessel is essential to obtain a good signal. If the tip region is misaligned, the Doppler spectrum does not correctly represent the velocity profile in the blood vessel. However, the intravascular Doppler ultrasound device 100 has the tip region 106 mechanically bendable in at least one direction perpendicular to the longitudinal direction L over an angular range illustrated by double arrow A in FIG. 1. The passive bending motion can be reversed. Suitable materials that allow passive bending of the tip region of the catheter body back and forth are as such well known in the art. Keeping in mind that other sections of the catheter body, which are not shown in FIG. 1, are suitably made of bendable material as well, the longitudinal extension of the bendable tip region can be adjusted to the requirements of a given application. There may be differences in the amount of bendability in different sections of the catheter body, and in different parts of the tip regions. In the present example, the full longitudinal extension of the tip region 106 shown in FIG. 1 is homogeneously bendable in two dimensions oriented perpendicular to the longitudinal direction L, thus opening a corresponding field of bending positions.

To achieve alignment, the intravascular Doppler ultrasonic device 100 further has an actuator 110 arranged in the bendable part of the tip region 106. The actuator 110 is configured to receive actuation drive power through the catheter body 102 from an actuator driver 112 and to exert to the tip region a bending moment of a controllable amount. A controller 114, which will be described in more detail further below, is configured to control the actuator driver 112 in the actuation drive power delivery to the actuator so as to control the amount of the bending moment exerted to the tip region 106.

Operation of the intravascular Doppler ultrasonic device 100 is illustrated in FIG. 1 by schematically showing a total of three exemplary bending positions of the tip region corresponding to three different orientations of ultrasound probe 108 in the tip region 106, as visualized by arrows L, B1, and B2. Of the three exemplary bending positions shown, thus, one maintains the tip region oriented along the longitudinal direction L and corresponds to the case of no bending or a bending angle of 0° of the tip region with respect to the longitudinal direction L; a second bending position has the tip region 106 bent with a first bending angle towards a lower wall section 116 of the blood vessel 104 and oriented along a direction B1 with an angle of approximately 45 degrees with respect to the longitudinal direction L in a first direction; a third bending position shown has the tip region 106 bent with a second bending angle towards an upper wall section 118 of the blood vessel 104 and oriented along a direction B2 with an angle of approximately 45 degrees with respect to the longitudinal direction L in an opposite second direction in comparison with the direction B1. It is noted that the bending in the schematic illustration of FIG. 1 is shown within only one plane parallel to the paper plane of FIG. 1. However, it can preferably be effected in two perpendicular planes. Such embodiments correspondingly comprise additional actuators, which are not shown in FIG. 1. Actuators for different planes of bending can advantageously be driven and controlled individually to achieve a wide range of possible bending positions of the tip region 106. It is noted that only one actuator 110 is shown in the schematic illustration of FIG. 1. This is only for reasons of a simple graphical representation. To cover a full desired range of bending positions two or more actuators may be required. More detail on this aspect will be discussed further below in the context of the description of FIGS. 7 to 10. In accordance with a given primary direction of ultrasound emission associated with a given bending position, and in dependence on the relative orientation of the directions L, B1 and B2 of the tip region with respect to the orientation of the blood vessel 104 at the insertion position of the ultrasound probe, there are different respective scan volumes 120, 122 and 124, from which an ultrasound echo is received. The scan volumes for the three different bending positions shown in FIG. 1 are represented schematically only by dashed rectangles. This illustration already shows that the bending positions B1 and B2 only partly use scan volumes inside the blood vessel, while most of the scan volumes are outside the blood vessel. No instructive Doppler information indicative of a velocity of particles in the blood as the ultrasound scattering medium in the blood vessel causing the ultrasound echo radiation can be obtained from regions outside the blood vessel. Thus, the Doppler spectrum data retrieved from the scan volumes 122 and 124 have poorer signal quality in comparison with the Doppler spectrum data retrieved from the scan volume 120, which is fully within the blood vessel 104. This effect is illustrated in FIG. 2, which shows two different Doppler spectra, in which the determined velocity of an ultrasound scattering medium in the blood vessel is plotted on a linear scale as a function of time for two different bending positions, one corresponding to the well aligned orientation L indicated in FIG. 1 (upper spectrum 126), and another to a misaligned orientation such as B1 or B2 (lower spectrum 128). Measured values are represented by dots, and an envelope line is shown by a continuous line in both graphs, indicating a respective maximum value as a common reference for both spectra 126 and 128 for each point in time. As can clearly be seen, velocity values measured in the lower spectrum 128 are generally lower than in the upper spectrum 126. This is indicative of echo data received from an area with lower blood velocity. This allows concluding that the lower spectrum is taken from a scan volume that includes a larger fraction of blood flowing close to the inner wall of the vessel, as it is illustrated for the scan volume 122 in FIG. 1. On the other hand, the upper spectrum 126 can be concluded to be taken from a scan volume that includes more fractions having a higher velocity of blood flow, which is typical for the volume fraction close to the center of the blood vessel, as it is the case for the scan volume 120. The above description shows that the alignment of the tip region 106 is important to obtain a good signal. If the bending position of the tip region 106 (sometimes also referred to as the Doppler angle) is too large, for instance due to bending of the tip region, two problems occur: the sample area is partly outside the blood vessel, namely in the surrounding tissue, and the sample volume is rotated with respect to a blood flow line corresponding to the longitudinal direction L in FIG. 1.

As a result, the Doppler spectrum does not fully represent the velocity profile in the blood vessel. Manual manipulation of the proximal end cannot fully resolve this problem. Therefore, the present embodiment provides the self-adapting tip region 106, which automatically finds the optimal Doppler angle and thus enables an easier and faster alignment procedure and a better signal.

Next, therefore, the controller 114 of the intravascular Doppler ultrasonic device 100 will be described in more detail with reference to FIG. 3. The controller 114 comprises a Doppler spectrum determination unit 130, which is configured to receive the probe signal and to determine therefrom Doppler spectrum data indicative of a Doppler spectrum of the ultrasound echo radiation. The Doppler spectrum is determined from the received probe signal by a Fourier transform. Suitably, this is implemented in the Doppler spectrum determination unit in the form of a Fast Fourier Transform (FFT) algorithm using the probe signal as an input. The Doppler spectrum is represented by the amount of the spectral power S of the received ultrasound echo radiation as a function of the frequency f of the ultrasound echo radiation.

For optional further analysis and display purposes, the Doppler spectrum determination unit is suitably also configured to determine a further representation of the Doppler spectrum in the form of the spectral power S of the received ultrasound echo radiation as a function of the velocity of an ultrasound scattering medium causing the ultrasound echo radiation. As is well known, the velocity can be determined from the Doppler frequency shift of the echo radiation with respect to a frequency of the emitted ultrasonic radiation.

A Doppler spectrum analysis unit 132 is configured to receive the Doppler spectrum data and to determine from it a Doppler signal quality measure indicative of a signal quality of the Doppler spectrum. The Doppler signal quality measure is determined using at least one of the following quantities:

- the Doppler zeroth moment of the spectral power of the received ultrasound echo radiation
- the Doppler first moment of the spectral power of the received ultrasound echo radiation,
- the Doppler second moment of the spectral power of the received ultrasound echo radiation,
- the resistivity index, or
- the pulsatility index.

The Doppler zeroth moment is indicative of the signal power of the received ultrasound echo radiation. It is defined as $$M_0 = \int S(f) df.$$

Here, $M_0$ denotes the Doppler zeroth moment, f denotes the frequency f of the ultrasound echo radiation, and S denotes the spectral power of the received ultrasound echo radiation.

The Doppler first moment is defined as $$M_1 = \int f \cdot S(f) df.$$

The Doppler first moment thus depends on a mean velocity of the scattering medium, such as blood.

The Doppler second moment is defined as $$M_2 = \int f^2 \cdot S(f) df$$

and thus provides information on an angle of the tip region relative to an axis of a lumen of the blood vessel.

The resistivity index is sometimes also called resistance index and often abbreviated as RI. It is a measure of pulsatile blood flow that reflects the resistance to blood flow caused in a vascular region distal to the site of measurement. It can for instance be determined as $$RI = (fMS - fD)/fMS,$$

wherein fMS is a maximum systolic Doppler frequency, and fD is a maximum Doppler frequency at the diastolic end.

The pulsatility index (PI) is equal to the difference between peak systolic velocity and the minimum diastolic velocity divided by the mean velocity during the cardiac cycle. As is well known, the blood velocity in arteries are higher during systole than during diastole. The pulsatility index decreases with increasing distance from the heart of the living being.

In some embodiments, only one of the mentioned quantities is used for determining the Doppler signal quality measure. An example of such a Doppler signal quality measure is the Doppler first moment. In other embodiments, the Doppler signal quality measure is determined from using a formula that includes two or more of these quantities. An example of such a Doppler signal quality measure is formed by a sum of the Doppler first moment and the Doppler second moment.

An actuation controller 134 is configured to control power delivery to the actuator so as to control the amount of the bending moment. The tip region 106 thus captures sample volumes under different Doppler angles. In particular, the actuation controller 134 is configured to determine the actuation drive power in dependence on the determined Doppler signal quality measure. This control of the orientation of the tip region 106 automatically finds an optimal angle based on finding a maximum of the Doppler signal quality measure in an available or pre-determined range of bending positions that can be scanned in an alignment process that even may be performed continuously to enable a re-alignment.

The Doppler spectrum data measured is processed for imaging purposes of a given application case and then displayed, either alone or in combination with further image data obtained by another imaging technique, using a display device 136.

Thus, the tip region 106 is mechanically active and automatically controllable to obtain most suitable Doppler spectrum data using the feedback provided by the determined Doppler signal quality measure.

In the prior art, for comparison, it has been considered difficult to achieve a tip alignment of an intravascular Doppler ultrasonic devices with respect to the blood vessel, in particular when using a thinner and thus more flexible, "floppy" catheter in order to access peripheral, small and tortuous blood vessels. This notion is due firstly to the catheter bending more easily due to external forces exerted by the blood flow or the vessel wall. Secondly, it is difficult to control the distal tip orientation by a manual manipulation at the proximal end of a "floppy" catheter device. The self-adapting tip region 106 of the intravascular Doppler ultrasonic device 100, however, does enable a tip alignment of such catheter devices in the more difficult constellations described and thus enables Doppler measurements even with floppy catheter devices.

In addition—or as an alternative—to using the Doppler spectrum as a source of feedback to automatically drive the actuator to the optimal bending position, the most suitable sample volume for data display or data analysis can be selected based on an analysis of the of the Doppler signal quality measure. This allows improving Doppler based imaging results.

Figure 4:
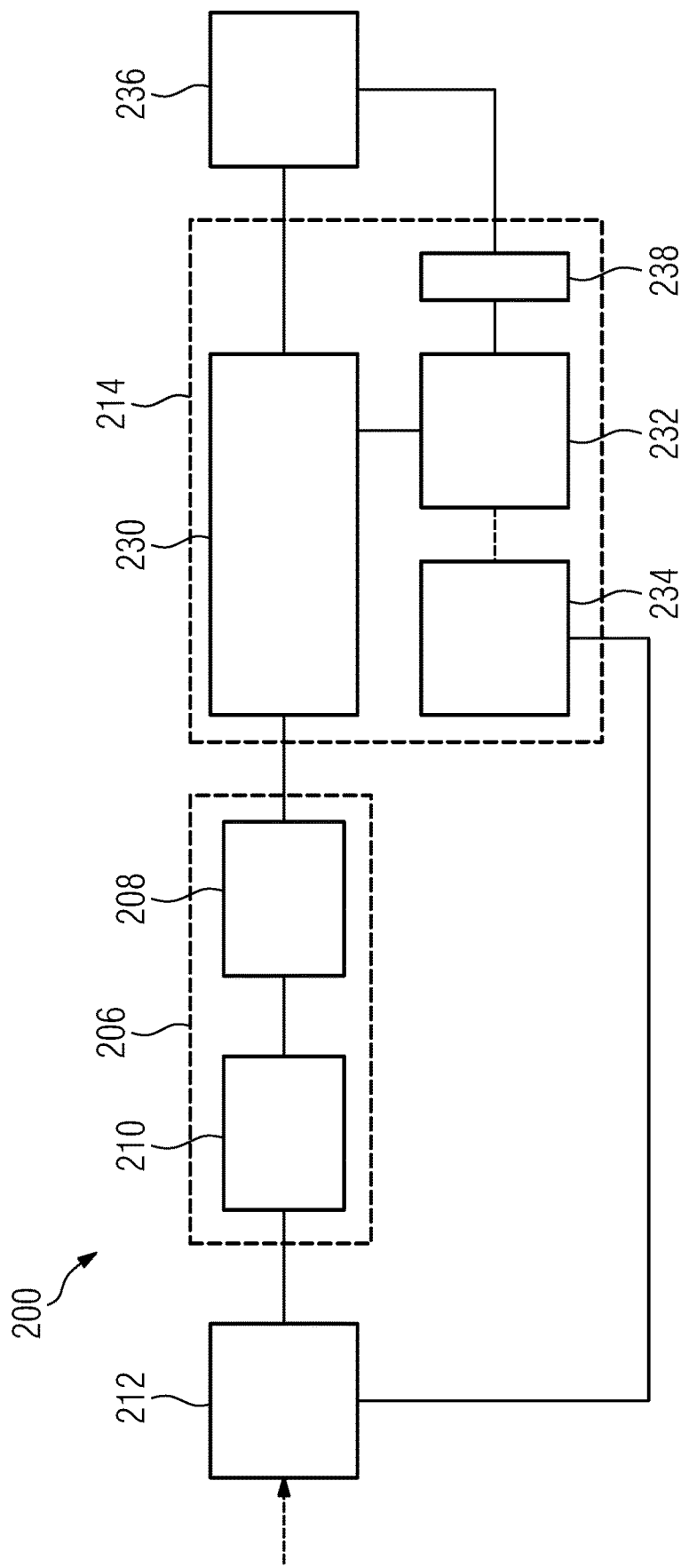
FIG. 4 is a block diagram of an intravascular Doppler ultrasonic device in accordance with a further embodiment of the present invention.

An intravascular Doppler ultrasonic device 200 enabling this additional or alternative feature will be described in the following with reference to FIG. 4, as a variant of the embodiment of FIGS. 1 to 3. FIG. 4 is a block diagram of the intravascular Doppler ultrasonic device. Reference labels used in FIG. 4 correspond to those used in FIGS. 1 to 3 except for the first digit, which is a "2" instead of a "1". This is to restrict the following description to the features distinguishing the embodiment of FIG. 4 from the embodiment of FIGS. 1 to 3. All other features of the elements and units that the intravascular Doppler ultrasonic device 200 of FIG. 4 has in common with the embodiments of FIGS. 1 to 3 can thus be easily found in the context of the detailed description of the earlier embodiment hereinabove.

In the intravascular Doppler ultrasonic device 200, the actuation controller 234 controls a bending motion of the tip region for continuously scanning across a range of different bending positions, and the Doppler spectrum determination unit 230 continuously provides the Doppler spectrum data determined for the different bending positions, which is analyzed by the Doppler spectrum analysis unit 232. An additional Doppler spectrum selection unit 238 is configured to select only that Doppler spectrum data which is associated with those bending positions that fulfill a predetermined Doppler spectrum selection criterion in terms of the Doppler signal quality measure, which is then received and displayed by the display device 236 that forms a graphical user interface. The Doppler spectrum selection criterion is for instance implemented as a lower threshold value or as an interval of the Doppler signal quality measure, which allows distinguishing between Doppler spectrum data to be discarded or to be selected for display.

This selection feature can optionally be provided even without using the feedback mechanism described for the embodiment of FIGS. 1 to 3, for instance by using a manual control of the actuator driver 212. This option is indicated by a dashed arrow representing the manual control option, and by a dashed line connecting the Doppler spectrum analysis unit 232 and the actuation controller 234.

The following description turns to embodiments making use of different hardware implementations for actuation of the bending motion in the tip region of the intravascular Doppler ultrasonic device of the present invention.

Figure 5:
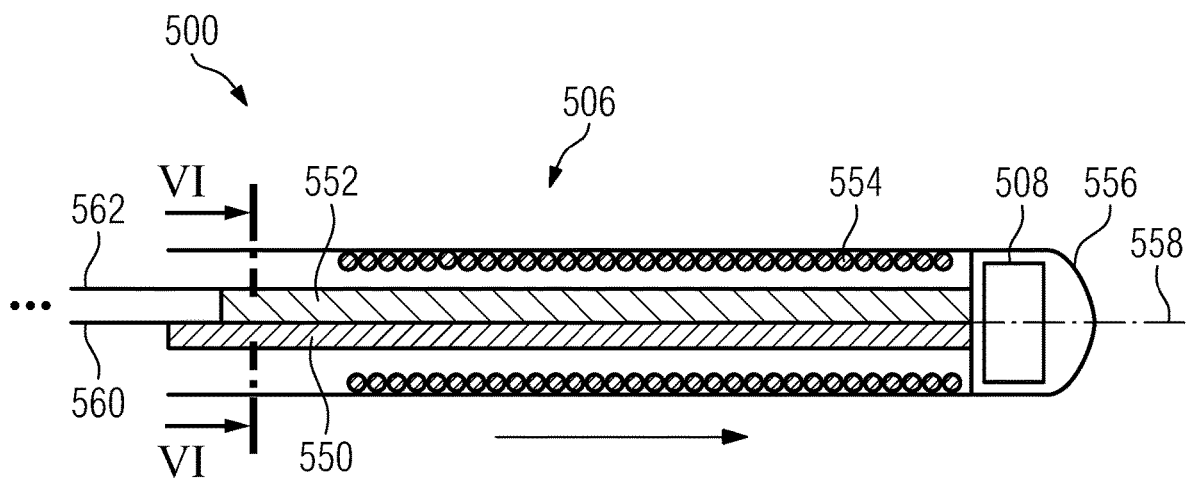
FIG. 5 is a schematic sectional view of a tip region of an intravascular Doppler ultrasonic device in accordance with a further embodiment of the present invention.
Figure 6:
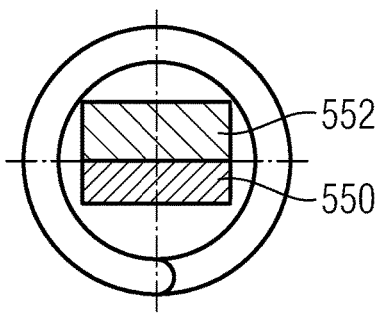
FIG. 6 is a further sectional view of the embodiment of FIG. 5 along the line VI-VI shown in FIG. 5.

FIG. 5 is a schematic sectional view of a tip region 506 of an intravascular Doppler ultrasonic device 500 in accordance with a further embodiment of the present invention. FIG. 6 is a further sectional view of the embodiment of FIG. 5 along the line VI-VI shown in FIG. 5. Both Figs. will be referred to in parallel in the following.

The tip region 506 comprises a metal core 550, which is thin and flat, for instance foil-like. An electroactive polymer (EAP) based actuator 552 is used as the actuator for exerting the bending moment and is attached to the metal core. Towards the distal end of the tip region 506, a coil 554 and an ultrasound transducer 508 is arranged. Ultrasound generated is provided via an ultrasound acoustic window 556. Suitably, the neutral line of the structure coincides with a device center line 558. The actuator is provided with actuation drive power through metal wires 560 and 562.

Advantages of using an EAP material layer in the actuator are its low power requirements, a fast noiseless, accurate and high resolution response, high mechanical flexibility, reversible actuation and the possibility of a direct electrical control and feedback. EAP material layers can be manufactured into a desired shape allowing integration into the tip region. Suitable electro active polymer materials for use with the present invention can be divided in field driven and ionic driven materials. Field driven EAP's are actuated by an electric field through direct electromechanical coupling. Examples of field driven EAP materials suitable for use in the present context are electrostrictive polymers such as dielectric elastomers, PVDF based relaxor polymers and liquid crystal elastomers (LCE). The actuation mechanism for ionic EAP materials involves a diffusion of ions. Examples of ionic driven EAP materials are conjugated polymers, carbon nanotube (CNT) polymer composites and Ionic Polymer Metal Composites (IPMC). Both classes have multiple family members.

A bending covering a range between two bending positions such as the bending positions B1 and B2 shown in FIG. 1 can be achieved by using a pre-shaped tip or a pre-stressed actuator.

As an example, using a single EAP actuator as shown in FIG. 5, bending from B1 to B2 can be achieved with a pre-curved actuator-core configuration. "Pre-curved" means the actuator-core configuration bends in one direction when the actuation drive power is zero. If the actuator-core configuration is designed to be not pre-curved but straight when the actuation drive power vanishes, the tip can only bend in one direction, for instance from an orientation along L to an orientation along B1 (or from L to B2). For the single EAP actuator expands in-plane when the drive power is increased from zero to a certain value and can thus exert a bending moment in only one direction. However, if the tip is pre-curved via geometry or a pre-stress, for instance to be oriented along B1 under vanishing actuation drive power, the tip can cover the range of orientations from B1 to B2 when the actuation drive power is increased from zero to a certain value. In this case, thus, a non-zero actuation drive power is needed to maintain the tip in a straight orientation along L. In this regard, using an EAP actuator is particularly advantageous because of its low power requirements.

Figure 7:
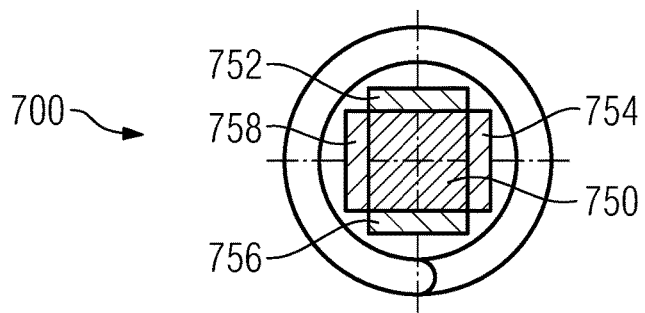
FIG. 7 is a further sectional view of a variant of the embodiment of FIG. 5.

In other embodiments having a straight orientation under vanishing actuation drive power, the bending of the tip region is suitably actuated by several actuators, which may be implemented as antagonist actuator pairs exerting bending moments in opposite directions. An example of this kind is shown by sectional view of a tip region of an intravascular Doppler ultrasonic device 700 in accordance with a further embodiment of the present invention. The sectional view of FIG. 7 is taken at a position of the tip region comparable to that used for FIG. 6. Here, antagonist actuator pairs 752, 756 and 754, 758 are attached to a metal core 756.

Figure 8:
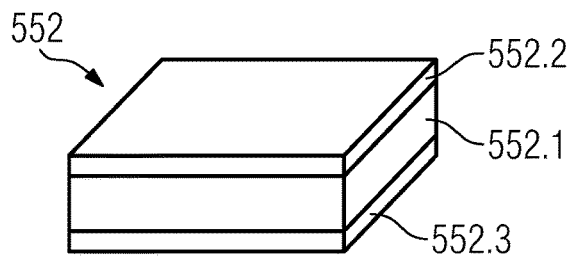
FIGS. 8 to 11 show schematic illustrations of an actuator suitable for use in the tip region of embodiments of the intravascular Doppler ultrasonic device, in a non-actuated (FIGS. 8, 10) and in an actuated state (FIGS. 9, 11)
Figure 9:
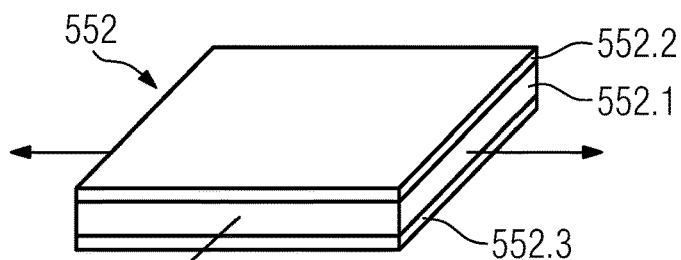
Figure 10:
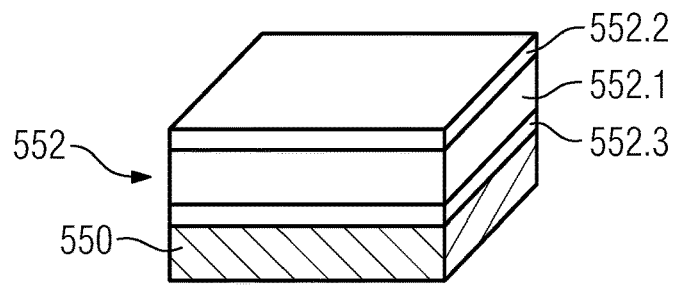
Figure 11:
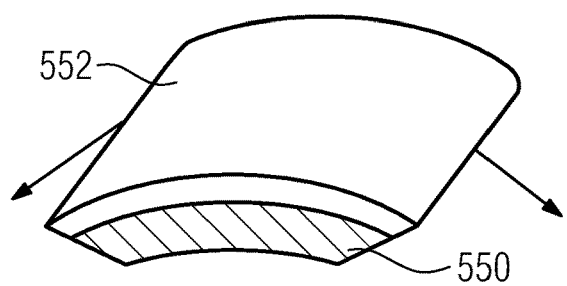

For explaining operation of the embodiment of FIGS. 5 and 6, additional reference is made to FIGS. 8 to 11. FIGS. 8 and 9 show schematic illustrations of the structure of an EAP actuator 552, which has an EAP material layer 552.1 embedded between two electrodes 552.2 and 552.3. FIG. 8 corresponds to a non-actuated state, and FIG. 9 to an actuated state of the EAP actuator 552. FIGS. 10 and 11 show schematic illustrations of the structure of an EAP actuator 552 and the metal core 550. When the EAP material layer 552.1 expands in-plane (cf. FIG. 9) due to electrical activation by the actuator driver (not shown in FIG. 5, but cf. FIGS. 1 to 4) via the electrodes 552.2 and 552.3, the structure formed by the EAP actuator 552 and the metal core 550 experiences a bending moment and bends the tip region 506 downward. To increase a force-stroke output a loosely stacked actuator assembly can be used. Multi-directional bending can be achieved by using two or more EAP actuators.

An ionic EAP material layer with increased stroke can be used in the EAP actuator 552 to obtain increased bending. The operation principle of increased stroke works as follows: An actuation voltage is used to power the actuation. At a maximum voltage corresponding to a maximum stroke of the EAP material layer, an AC voltage is applied to briefly heat the EAP material to a temperature above the Tg of the polymer, release the DC actuation voltage and let the EAP cool back down to below the Tg. This sets the EAP in a new starting position from which a new actuation can be initiated. This increases the stroke of the EAP material by almost 100% every time the 'reset' is performed. Driving this process is fully electronic. No extra hardware parts need to be added in the in the catheter tip region. Due to the small size of the EAP component the heating and cooling is rapid. The heat will affect only the EAP material. A patient is protected by an insulation of the catheter tip.

In addition to or as an alternative to using an EAP based actuator, the actuator 552 can use a shape memory alloy (SMA) wire which is connected with the thin metal core 550. Upon heating by electrical current the SMA alters it shape. Two shape-change options are suitable: bending (when intrinsically programmed in the material), and shortening. In both cases the structure formed by the SMA based actuator 552 and the metal core 550 will bend in one direction. Multi-directional bending can be achieved by using two or more SMA actuators. The actuation is one-way from a first shape (soft phase) to a second shape (hard phase). Intermediate actuations in between the first and second shape can be achieved by stopping the heating process precisely in between the transition from the soft to the hard phase. While SMA actuators are generally not considered easy for use in catheters and guide wires, the present invention advantageously provides feedback information in the form of the Doppler signal quality measure for precisely controlling their operation. Reverse actuation is achieved by cooling of the SMA material, upon which the material softens and the metal core 550 acts as antagonist. The metal core 550 can also be a super elastic SMA. Also the coil is designed in one variant to act as an antagonist.

The SMA transition temperature is suitably chosen such that the outer diameter (coil) stays below 45° C. to avoid coagulation of blood. The main advantage of SMA are its strength against actuator stress and related small form factors.

As for an SMA the required force and stroke is small it is also an option to use the two-way effect of a trained SMA actuator. In that case the core can be less stiff as it does not have apply a force to reset the SMA to its original position.

It is also an option to replace the metal core by a SMA in the active region. The SMA is then slightly off the central axis to cause a bending. The coil can act as an antagonist or again a two-way actuation can be applied.

It is also an option to apply two SMA actuators for one-way or two-way actuation, both arranged off center without a core. This enables a symmetrical (low) stiffness and bending in two directions.

To increase the precision of the actuator 552, an EAP material layer can be laminated to an SMA actuator. The EAP material can be used to fine-tune the actuation: The SMA actuator provides coarse deformation, and the EAP material layer provides a fine resolution deformation on top, to adjust the coarse setting of the SMA actuation.

Alternatively, in certain cases the EAP material can additionally act as an antagonist for the SMA actuator.

The interface between SMA and metal core is electrically (and thermally) insulated. The current can flow through the core wire, then through the SMA section and back through a single Cu wire. The SMA actuator can also be a folded wire that is electrically connected at both proximal sections.

A further option for implementing the actuator is based on similar principle as in the case of using EAP material, but involves using another material in the form of a thermal expansion actuator such as a bi-metal formed of two different metals with different coefficients of thermal expansion (CTE). The first metal can be the metal core 550. The second metals should then have a thermal expansion coefficient which is at least a factor of two larger than the CTE of the metal core 550. The bi-metal can be designed to be straight at room temperature, or at body temperature. The two metal elements of the bimetal can be separated by a thin thermally insulating layer, enabling bending in two directions.

This can for instance be realized by manufacturing the metal core 550 from a low expansion material such as Invar alloy (Fe36Ni), which can be tailored to have an effective CTE of 1.2 ppm/° C. at body temperature (as compared to for instance aluminum which has a CTE of 23).

Figure 12:
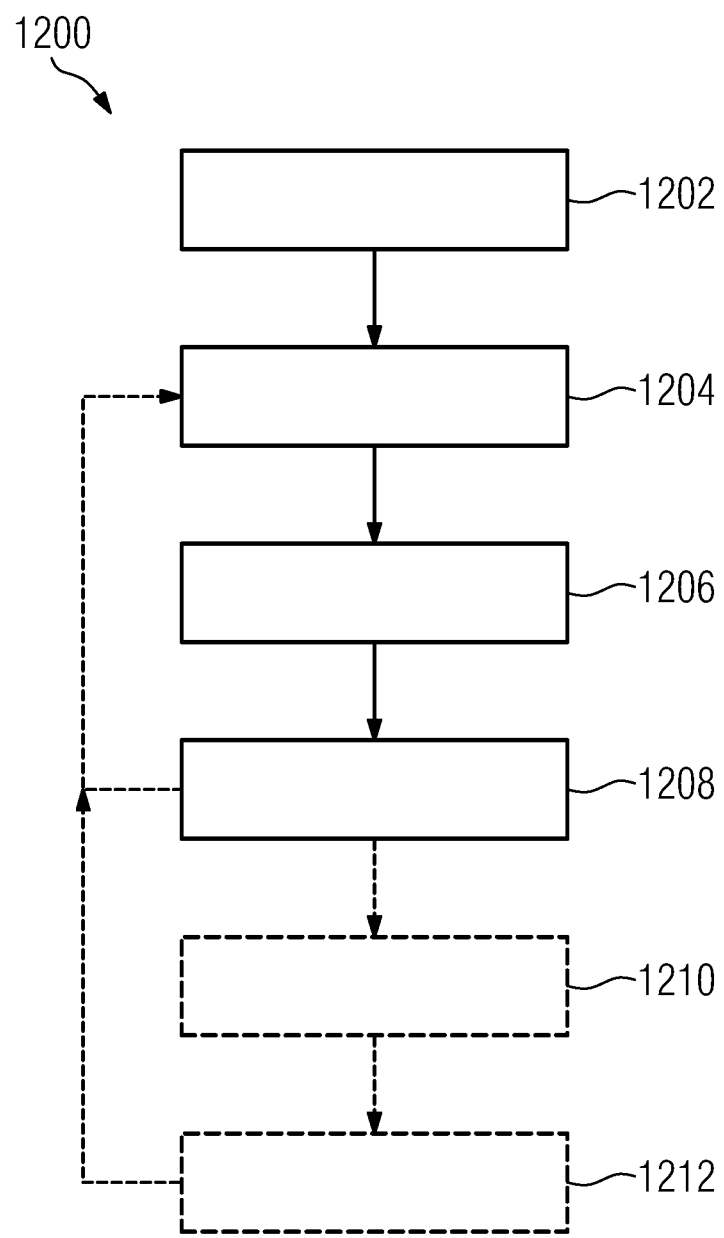
FIG. 12 is a flow diagram of an embodiment of a method for controlling operation of an intravascular Doppler ultrasonic device.

FIG. 12 is a flow diagram of an embodiment of a method 1200 for controlling operation of an intravascular Doppler ultrasonic device.

The method 1200 comprises, in a step 1202, controlling emission of ultrasonic radiation by an ultrasound probe from a distal end of a catheter body in substantially a longitudinal direction of the catheter body, for receiving ultrasound echo radiation from substantially the longitudinal direction, and receiving a probe signal indicative thereof.

In a step 1204, Doppler spectrum data is determined and provided using the probe signal.

As explained hereinabove, the tip region of the catheter is bendable in at least one direction perpendicular to the longitudinal direction. An actuator driven by actuation drive power delivery can drive exertion of a bending moment of a controllable amount to the tip region. To achieve automatic control of the actuation power delivery, a Doppler signal quality measure indicative of a signal quality of the Doppler spectrum is determined (step 1206). In a subsequent step 1208, the actuation drive power for the actuator in the tip region is determined and delivered to the actuator.

In the following, options for extending or varying the method 1200 will be described.

In case of a continuous monitoring and tip alignment, the ultrasound probe provides a stream of probe signals. The method thus suitably branches back from determining and delivering the actuation drive power (step 1208) to performing a next iteration of steps 1204 to 1208, i.e. determining Doppler spectrum data (step 1204) and the Doppler signal quality measure (step 1206), for maintaining continuous monitoring of the Doppler spectrum and continuously performing or maintaining the alignment according to step 1208 of the tip region with the blood vessel.

In addition to automatically controlling the orientation tip region with respect to the blood vessel, the method may additionally comprise selecting only that Doppler spectrum data which is associated with those scanned bending positions that fulfill a predetermined Doppler spectrum selection criterion in terms of the Doppler signal quality measure (step 1210), and controlling, in step 1212, the display of the selected Doppler spectrum data via a graphical user interface.

The method can be implemented in the form of performing software running on a suitable equipped programmable processor or computer, or under control of application specific integrated circuit or a field programmable array.

In summary, an intravascular Doppler ultrasonic device comprises a tip region forming a fraction of a catheter body at a distal end thereof and carrying an ultrasound probe. The tip region is bendable in a direction perpendicular to a longitudinal direction. An actuator is provided in the tip region, which is configured to receive actuation drive power provided through the catheter body and to exert to the tip region a bending moment of a controllable amount. An actuation controller is configured to control actuation drive power delivery to the actuator so as to control the amount of the bending moment. A Doppler spectrum analysis unit is configured to receive Doppler spectrum data and to determine from it a Doppler signal quality measure indicative of a signal quality of the Doppler spectrum. The actuation controller is configured to determine the actuation drive power in dependence on the determined Doppler signal quality measure.

Other variations to the disclosed embodiments can be understood and effected by those skilled in the art in practicing the claimed invention, from a study of the drawings, the disclosure, and the appended claims. For instance, the disclosed intravascular Doppler ultrasonic device can be implemented with a catheter body either in the form of a hollow catheter or of a guidewire.

In the claims, the features and functions of the intravascular Doppler ultrasonic device are described with respect to an elongated state of the catheter body for the purpose of providing a reference for definition. In particular, the claims are not to be understood in a sense that the direction in space of emission of ultrasound radiation from the tip region must remain identical irrespective of a direction and amount of bending of the catheter body or of the tip region.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An intravascular Doppler ultrasonic device, comprising:
   a catheter body shaped for intravascular insertion into a blood vessel of a living being, wherein the catheter body comprises:
      a tip region forming a fraction of the catheter body at a distal end thereof; and
      a region proximal of the tip region and extending along a longitudinal direction, wherein the tip region is bendable in at least one direction perpendicular to the longitudinal direction;
   an ultrasound probe in the tip region, which is configured to emit ultrasonic radiation from the distal end of the catheter body and to receive ultrasound echo radiation and provide a probe signal indicative thereof, wherein the ultrasound echo radiation comprises a Doppler frequency shift;
   a Doppler spectrum determination unit, which is configured to receive the probe signal and to determine therefrom a Doppler spectrum data indicative of a Doppler spectrum of the ultrasound echo radiation;
   an actuator in the tip region, which is configured to receive actuation drive power provided through the catheter body and to exert to the tip region a bending moment of a controllable amount;
   an actuation controller, which is configured to control actuation drive power delivery to the actuator so as to control the amount of the bending moment;
   a Doppler spectrum analysis unit, which is configured to receive the Doppler spectrum data and to determine from it a value of a Doppler signal quality measure indicative of a signal quality of the Doppler spectrum, wherein the Doppler signal quality measure is different from the Doppler frequency shift;
   wherein the actuation controller is further configured:
      to determine the actuation drive power in dependence on the determined value of the Doppler signal quality measure;
      to control a scanning motion of the tip region within a predetermined scanning range by controlling the actuator for consecutively setting a plurality of bending moments;
      to associate each bending moment of the plurality of bending moments with a different value of the Doppler signal quality measure;

to determine, based on the determined value of the Doppler signal quality measure, whether the signal quality of the Doppler spectrum exceeds a threshold; and to determine the bending moment to be used for operation by selecting a bending moment which is associated with the determined value of the Doppler signal quality measure.

2. The intravascular Doppler ultrasonic device of claim 1, wherein the Doppler spectrum analysis unit is configured to determine the value of the Doppler signal quality measure at least once per cardiac cycle of the living being, and wherein the actuation controller is configured to adjust the bending moment in a subsequent cardiac cycle if the signal quality of the Doppler spectrum exceeds the threshold.

3. The intravascular Doppler ultrasonic device of claim 1, wherein the Doppler spectrum analysis unit is configured to determine the value of the Doppler signal quality measure by determining and using at least one of the following quantities for calculating the Doppler signal quality measure:
  a Doppler zeroth moment of the spectral power of the received ultrasound echo radiation;
  a Doppler first moment of the spectral power of the received ultrasound echo radiation;
  a Doppler second moment of the spectral power of the received ultrasound echo radiation;
  a pulsatile index, or
  a resistive index.

4. The intravascular Doppler ultrasonic device of claim 1, wherein the ultrasound probe is configured to emit the ultrasonic radiation and provide the probe signal continuously.

5. The intravascular Doppler ultrasonic device of claim 4,
  wherein the actuation controller is configured to control a bending motion of the tip region for continuously scanning across a range of different bending positions; and
  wherein the Doppler spectrum determination unit is configured to continuously provide the value of the Doppler spectrum data determined for the different bending positions;
  further comprising:
    a Doppler spectrum selection unit, which is configured to select only that Doppler spectrum data which is associated with those bending positions that result in a signal quality of the Doppler spectrum that exceeds the threshold; and
    a graphical user interface, which is configured to receive and display the selected Doppler spectrum data.

6. The intravascular Doppler ultrasonic device of claim 1, wherein the actuation controller is configured to control a bending motion of the tip region across a range of bending positions, to determine a motion response measure indicative of a difference between the values of the Doppler signal quality measure determined at different ones of the bending positions, and to interpolate to the optimal velocity profile.

7. The intravascular Doppler ultrasonic device of claim 1, wherein the actuator comprises an electrically controllable shape-changing material, which is mechanically coupled to the catheter body in the tip region and configured to cause the bending moment by a shape change in response to receiving the actuation power.

8. The intravascular Doppler ultrasonic device of claim 7, wherein the actuator comprises at least one actuator layer made of an electroactive polymer material that is attached to a flat catheter core of the catheter body, and wherein the actuator layer is configured to expand in-plane in response to receiving the actuation power.

9. The intravascular Doppler ultrasonic device of claim 7, wherein the actuator comprises at least one actuator wire made of a shape memory alloy that is attached to a catheter core, and wherein actuator wire is configured to change its temperature in an amount that depends on an amount of actuation power received, and to change its shape in response to the temperature change.

10. The intravascular Doppler ultrasonic device of claim 7, wherein the actuator comprises at least one actuator layer made of a bi-metal that is attached to a flat catheter core of the catheter body, and wherein the actuator layer is configured to expand in-plane in response to receiving the actuation power.

11. The intravascular Doppler ultrasonic device of claim 1, wherein the actuator comprises at least one first actuator layer made of an electroactive polymer material that is attached to at least one second actuator layer made of a shape memory alloy.

12. A method for controlling operation of an intravascular Doppler ultrasonic device, the method comprising:
  controlling emission of ultrasonic radiation by an ultrasound probe from a distal end of a catheter body, for receiving ultrasound echo radiation, and receiving a probe signal indicative thereof, wherein the ultrasound echo radiation comprises a Doppler frequency shift;
  determining and providing Doppler spectrum data from the probe signal, the Doppler spectrum data being indicative of a Doppler spectrum of the ultrasound echo radiation;
  controlling actuation drive power delivery to an actuator in a tip region forming a fraction of the catheter body at the distal end thereof, wherein the catheter body comprises:
    the tip region; and
    a region proximal of the tip region and extending along a longitudinal direction, wherein the tip region is bendable in at least one direction perpendicular to the longitudinal direction, so as to drive exertion of a bending moment of a controllable amount to the tip region; and
  wherein controlling actuation power delivery comprises:
    receiving the Doppler spectrum data and determining from it a value of a Doppler signal quality measure indicative of a signal quality of the Doppler spectrum, wherein the Doppler signal quality measure is different from the Doppler frequency shift,
    determining the actuation drive power in dependence on the determined value of the Doppler signal quality measure;
    controlling a scanning motion of the tip region within a predetermined scanning range of different bending positions by controlling the actuator for consecutively setting a plurality of bending moments;
    associating each bending moment of the plurality of bending moments with a different value of the Doppler signal quality measure;
    determining, based on the determined value of the Doppler signal quality measure, whether the signal quality of the Doppler spectrum exceeds a threshold; and determining the bending moment to be used for operation by selecting that bending moment which is associated with the determined value of the Doppler signal quality measure.

13. The method of claim 12, further comprising:
controlling a bending motion of the tip region for continuously scanning across the scanning range;
providing the Doppler spectrum data determined for the different bending positions;
selecting only that Doppler spectrum data which is associated with that bending position which is associated with the determined value of the Doppler signal quality measure indicative of the highest Doppler signal quality; and
controlling display of the selected Doppler spectrum data via a graphical user interface.

14. A computer program for controlling operation of an intravascular Doppler ultrasonic device, comprising executable code for executing the method of claim 12 when executed by a processor of a computer.

\* \* \* \* \*